(12) United States Patent
Bediz et al.

(10) Patent No.: US 9,256,939 B1
(45) Date of Patent: Feb. 9, 2016

(54) SYSTEM AND METHOD FOR ALIGNING MAMMOGRAPHY IMAGES

(71) Applicant: Agfa HealthCare, Mississauga (CA)

(72) Inventors: Mehmet Bediz, Waterloo (CA); Ronald Dale Hitzelberger, Greenville, SC (US)

(73) Assignee: AGFA Healthcare, Ontario (CA)

( * ) Notice: Subject to any disclaimer, the term of this patent is extended or adjusted under 35 U.S.C. 154(b) by 15 days.

(21) Appl. No.: 14/334,522

(22) Filed: Jul. 17, 2014

(51) Int. Cl.
*G06K 9/00* (2006.01)
*G06T 7/00* (2006.01)
*G06K 9/62* (2006.01)
*G06K 9/52* (2006.01)
*G06T 3/00* (2006.01)
*G06K 9/46* (2006.01)

(52) U.S. Cl.
CPC ............ *G06T 7/0012* (2013.01); *G06K 9/4604* (2013.01); *G06K 9/52* (2013.01); *G06K 9/6267* (2013.01); *G06T 3/00* (2013.01); *G06T 2207/30068* (2013.01)

(58) Field of Classification Search
USPC .......................................................... 382/132
See application file for complete search history.

(56) References Cited

U.S. PATENT DOCUMENTS

| 5,825,936 | A | 10/1998 | Clarke et al. |
| 7,046,860 | B2 | 5/2006 | Soubelet et al. |
| 7,203,348 | B1 | 4/2007 | Karssemeijer et al. |
| 7,885,443 | B2 * | 2/2011 | Zingaretti et al. .... G06T 7/0014 382/128 |
| 2004/0161141 | A1 | 8/2004 | Dewaele et al. |

| 2004/0213447 | A1 | 10/2004 | Roehrig et al. |
| 2006/0050944 | A1 | 3/2006 | Takeo et al. |
| 2006/0110068 | A1 | 5/2006 | Luo et al. |
| 2006/0159321 | A1 | 7/2006 | Takeo et al. |
| 2006/0177125 | A1 | 8/2006 | Chan et al. |
| 2007/0122021 | A1 | 5/2007 | Zingaretti et al. |
| 2007/0206844 | A1 | 9/2007 | Russakoff et al. |
| 2011/0222752 | A1 | 9/2008 | Zhang et al. |
| 2008/0285825 | A1 | 11/2008 | Zhang et al. |

(Continued)

FOREIGN PATENT DOCUMENTS

| EP | 0610605 A1 | 8/1994 |
| EP | 0742536 A1 | 11/1996 |

(Continued)

OTHER PUBLICATIONS

Kom, Guillaume, et al., "Automated detection of masses in mammograms by local adaptive thresholding", Computers in Biology and Medicine, Oct. 20, 2006, pp. 37-48, vol. 37, New York, USA.

(Continued)

*Primary Examiner* — Yon Couso
(74) *Attorney, Agent, or Firm* — Lewis Rice LLC

(57) ABSTRACT

A method and system of aligning plurality of physically scaled mammography images within at least one viewport comprising: categorizing each mammography image to a corresponding mammography view; determining the image dimensions of each image based on the pixel spacing; choosing a first mammography image for each mammographic view based on the image dimensions; centering the first mammography image of each mammographic view within the at least one viewport; generating a virtual line across the at least one viewport along a boundary of the first mammography image; and aligning subsequent mammography images of the same mammographic view such that a boundary of the mammography image is aligned to the virtual line.

17 Claims, 10 Drawing Sheets

(56) References Cited

U.S. PATENT DOCUMENTS

| | | | |
|---|---|---|---|
| 2009/0060300 | A1 | 3/2009 | Neemuchwala et al. |
| 2010/0104148 | A1 | 4/2010 | Bovik et al. |
| 2011/0128289 | A1 | 6/2011 | Zingaretti et al. |
| 2011/0216949 | A1 | 9/2011 | Yang |
| 2012/0189175 | A1* | 7/2012 | Highnam et al. ..... G06T 7/0012 382/128 |

FOREIGN PATENT DOCUMENTS

| | | |
|---|---|---|
| EP | 0887769 A1 | 12/1998 |
| EP | 1256907 A1 | 11/2002 |
| EP | 2631873 A1 | 8/2013 |
| WO | 9928853 A1 | 6/1999 |
| WO | 0215113 A2 | 2/2002 |
| WO | 2013093687 A1 | 6/2013 |

OTHER PUBLICATIONS

Bhangale, Tushar, et al., "An unsupervised scheme for detection of microcalcifications on mammograms", IEEE International Conference on Image Processing, Sep. 10, 2000, pp. 184-187, vol. 1, Piscataway, NJ, USA.

Wang, Ted C., et al., "Detection of Microcalcifications in Digital Mammograms Using Wavelets", IEEE Transactions on Medical Imaging, Aug. 1, 1998, p. 498-509, vol. 17, No. 4, IEEE Service Center, Piscataway, NJ, USA.

Strickland, Robin N. et al., "Wavelet Transforms for Detecting Microcalcifications in Mammograms," IEEE Transactions on Medical Imaging, Apr. 1, 1996, pp. 218-229, vol. 15, No. 2, IEEE Service Center, Piscataway, NJ, USA.

Cheng, H.D., et al., "Computer-aided detection and classification of microcalcifications in mammograms: a survey," Pattern Recognition Society, Dec. 1, 2003, pp. 2967-2991, vol. 36, No. 12, Elsevier, Great Britain.

Sun, Yajie, et al., "A new approach for breast skin-line estimation in mammograms," Pattern Analysis and Applications, Apr. 4, 2006, pp. 34-47, vol. 9, Issue 1, Springer-Verlag, London, England.

Zheng, Bin, et al., "Multiview-based computer-aided detection scheme for breast masses," Medical Physics, Aug. 16, 2006, pp. 3135-3143, vol. 33, No. 9, Melville, NY, USA.

Marti, Robert, et al., "Breast Skin-Line Segmentation Using Contour Growing," Pattern Recognition and Image Analysis, Lecture Notes in Computer Science (LNCS), Jun. 6, 2007, pp. 564-571, vol. 4478, Springer-Verlag, Berlin Germany.

Kus, Pelin, et al., "Fully automated gradient based breast boundary detection for digitized X-ray mammograms," Computers in Biology and Medicine, Oct. 24, 2011, pp. 75-82, vol. 42, Issue 1, New York, NY, USA.

Pu, Jiantao, et al., "An ellipse-fitting based method for efficient registration of breast masses on two mammographic views," Medical Physics, Jan. 14, 2008, pp. 487-494, vol. 35, No. 2, Melville, NY, USA.

Honghong, Chen, "A Fast Classification Mask Construction Algorithm for Digital Mammograms," Journal of Convergence Information Technology, Jan. 31, 2012, pp. 483-488, vol. 7, No. 1, AICIT, Korea.

Rangarajan, Anand, et al., "A robust point matching algorithm for autoradiograph alignment," Visualization in biomedical computing : 4th international conference, VBC' 96, Sep. 22, 1996, pp. 277-286, vol. 1131, Hamburg, Germany.

* cited by examiner

SYSTEM AND METHOD FOR ALIGNING MAMMOGRAPHY IMAGES

BACKGROUND

1. Field of the Invention

The embodiments described herein relate to a system and method for image analysis and in particular to a system and method for the alignment of a plurality of physically scaled mammography images.

2. Description of the Related Art

Medical personnel (e.g. radiologists) examine mammography images to identify various abnormalities in a breast. The task of analyzing mammography images in a digital mammography system typically comprises of using a digital workstation with a display or viewport to align a pair of breast images acquired during a mammography study and comparing breast tissue images of the same side (left/right breast only) or symmetric sides (left and right breasts). The images used for comparison, while of the same object, may be acquired at different times, acquired with different imaging systems and/or acquired using different display settings. As such, medical personnel desire mammography systems that facilitate efficient diagnostic reviews of mammography images, regardless of its provenance, so as to allow them to quickly compare and detect differences between mammographic images and report their findings within clinically acceptable time frames.

Different types of image alignment protocols are employed for displaying mammography images of the breast for comparison. For example, one alignment protocol for images in the cranio-caudal ("CC") view may involve placing the left and right CC breast views next to each other so that the chest walls will meet on the central vertical axis of the viewport. Similar arrangements, known to those skilled in the art, also exist for medio-lateral oblique ("MLO") views. Other image alignment strategies include alignment based on anatomical features of the breast. In CC images, for example, the nipple located in each pair of images may be positioned so that they are horizontally aligned, that is, at the same height. For MLO images, either the nipple or pectoralis may be chosen as features used for alignment.

In general, the requirements with respect to mammographic images comparison are: 1) aligning the breast view so as to make the image comparison process easier and more efficient; 2) displaying mammographic images in the same physical scale such that a corresponding real object in each image is observed as the same size; and 3) ensuring that mammographic images are not panned so as to have image areas corresponding to breast tissue being partially outside the viewport or invisible to the examiner.

While currently employed alignment strategies satisfy the above listed requirements, these methods often result in reduced image symmetry, making image comparisons more time consuming. It is preferable to align images to achieve maximum symmetry so that they resemble mirrored images allowing the eyes and brain to quickly identify differences between images. Furthermore, breast features being obscured or missing due to the positioning of the breast during image acquisition may also make alignments relying on those features difficult or impossible. Consequently, a more robust and reliable alignment scheme is desirable. As described herein, a method and system for centering and aligning mammography images may provide greater symmetry is presented, thereby facilitating easier and faster side-by-side comparison.

SUMMARY

The following is a summary of the invention in order to provide a basic understanding of some aspects of the invention. This summary is not intended to identify key or critical elements of the invention or to delineate the scope of the invention. The sole purpose of this section is to present some concepts of the invention in a simplified form as a prelude to the more detailed description that is presented later.

Because of these and other problems in the art, the embodiments described herein provide in one aspect, a method for aligning a plurality of physically scaled mammography images within at least one viewport. The method comprising: categorizing each of the plurality of physically scaled mammography images based on a corresponding mammography view; determining image dimensions of each of the plurality of physically scaled mammography images based on pixel spacing; selecting a first mammography image from the plurality of physically scaled mammography images for each corresponding mammography view based on the image dimensions; centering the first mammography image within the at least one viewport; generating a virtual line across the at least one viewport based on a boundary of the first mammography image; and aligning each of the plurality of physically scaled mammography images corresponding to the mammography view such that a boundary of each of the plurality of physically scaled mammography images is aligned with the virtual line.

The embodiments described herein provide in another aspect, the method wherein the first mammography is vertically centered within the viewport.

The embodiments described herein provide in another aspect, the method wherein the virtual line is a horizontal virtual line.

The embodiments described herein provide in another aspect, the method wherein the boundary of the first mammography image consists of one of the following: a top boundary, a bottom boundary, a left boundary, and a right boundary.

The embodiments described herein provide in another aspect, the method wherein the boundary of each of the plurality of physically scaled images consists of one of the following: a top boundary, a bottom boundary, a left boundary, and a right boundary.

The embodiments described herein provide in another aspect, the method wherein the plurality of physically scaled mammography images in the corresponding mammography view contains at least one right mammography image associated with at least one left mammography image, and wherein aligning each of the plurality of physically scaled mammography images further comprises aligning the at least one right mammography image with the at least one associated left mammography image.

The embodiments described herein provide in another aspect, the method wherein the image dimensions are selected from a group consisting of: image height and image width.

The embodiments described herein provide in another aspect, the method wherein the first mammography image is selected based on the largest image dimensions.

The embodiments described herein provide in another aspect, the method wherein the plurality of mammography images each comprise a breast image region and wherein the image dimensions are determined based on the breast image region.

The embodiments described herein provide in another aspect, the method wherein the plurality of mammography images include a first temporal image and an associated second temporal image, and wherein aligning each of the plurality of mammography images further comprises aligning the first temporal image with the associated second temporal image.

The embodiments described herein provide in another aspect, the method wherein the pixel spacing is based on one of the following: a patient body coordinate system and a plate coordinate system.

The embodiments described herein provide in another aspect, a physical non-transitory computer readable medium comprising instructions for aligning a plurality of physically scaled mammography images within at least one viewport, the instructions comprising: categorizing each of the plurality of physically scaled mammography images based on a corresponding mammography view; determining image dimensions of each of the plurality of physically scaled mammography images based on pixel spacing; selecting a first mammography image from the plurality of physically scaled mammography images for each corresponding mammography view based on the image dimensions; centering the first mammography image within the at least one viewport; generating a virtual line across the at least one viewport based on a boundary of the first mammography image; and aligning each of the plurality of physically scaled mammography images corresponding to the mammography view such that a boundary of each of the plurality of physically scaled mammography images is aligned with the virtual line.

The embodiments described herein provide in another aspect, the physical non-transitory computer readable medium wherein the first mammography image is vertically centered within the viewport.

The embodiments described herein provide in another aspect, the physical non-transitory computer readable medium wherein the virtual line is a horizontal virtual line.

The embodiments described herein provide in another aspect, a system for aligning a plurality of physically scaled mammography images within at least one viewport, the system comprising: a memory for the plurality of physically scaled breast images; a processor configured to: categorize each of the plurality of physically scaled mammography images based on a corresponding mammography view; determine image dimensions of each of the plurality of physically scaled mammography images based on pixel spacing; select a first mammography image from the plurality of physically scaled mammography images for each corresponding mammography view based on the image dimensions; center the first mammography image within the at least one viewport; generate a virtual line across the at least one viewport based on a boundary of the first mammography image; and align each of the plurality of physically scaled mammography images corresponding to the mammography view such that a boundary of each of the plurality of physically scaled mammography images is aligned with the virtual line.

The embodiments described herein provide in another aspect, the system wherein the first mammography image is vertically centered within the viewport.

The embodiments described herein provide in another aspect, the system wherein the virtual line is a horizontal virtual line.

Further aspects and advantages of the embodiments described herein will appear from the following description taken together with the accompanying drawings.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment.

Figure 1A:
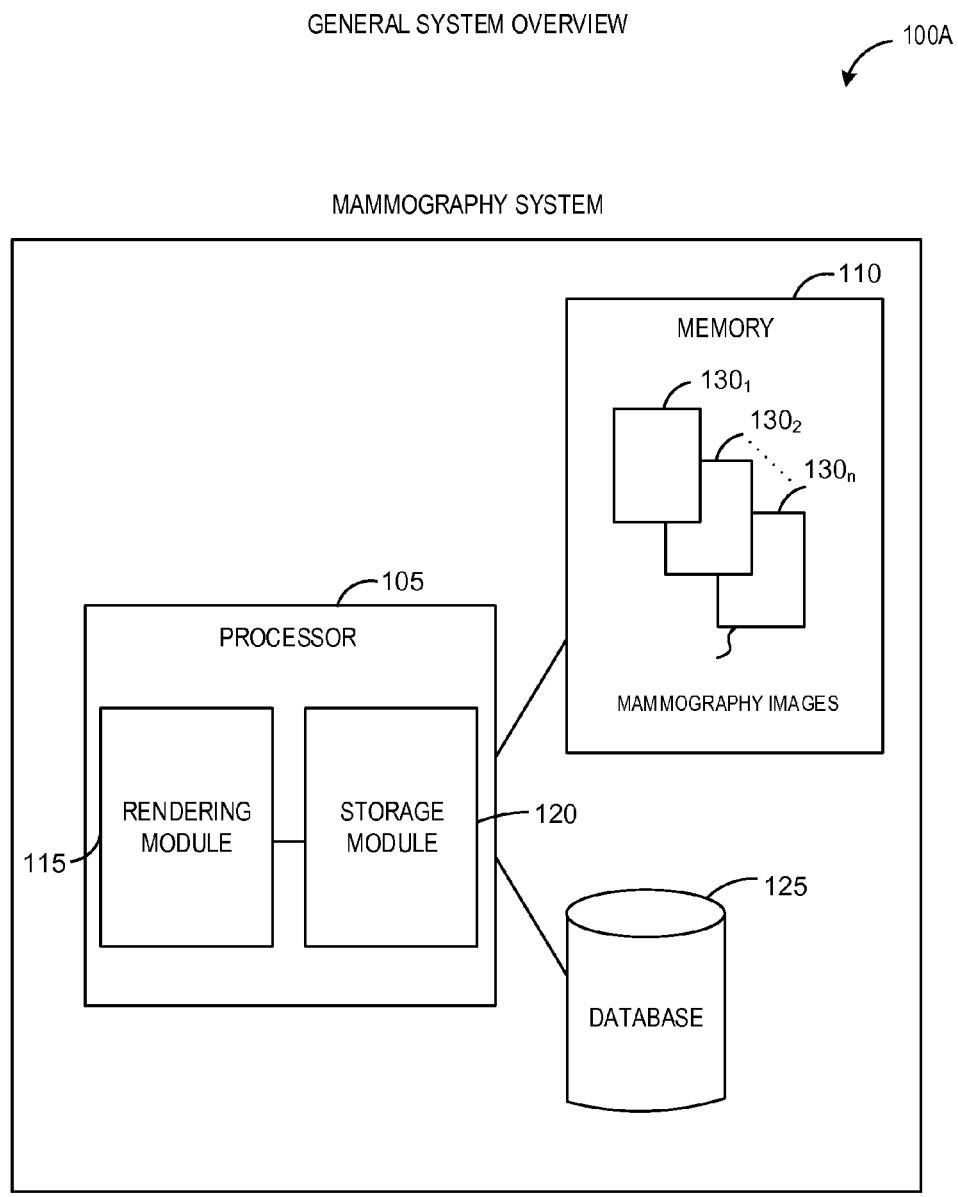
FIG. 1A is a block diagram of a mammography system.

The skilled person in the art will understand that the drawings, described below, are for illustration purposes only. The drawings are not intended to limit the scope of the applicants' teachings in anyway. Also, it will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF THE PREFERRED
EMBODIMENT(S)

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein. Where considered appropriate, for simplicity and clarity of illustration, reference numerals may be repeated among the figures to indicate corresponding or analogous elements or steps.

The embodiments of the systems and methods described herein may be implemented in hardware or software, or a combination of both. However, preferably, these embodiments are implemented in computer programs executing on programmable computers each comprising at least one module component which comprises at least one processor (e.g. a microprocessor), a data storage system (including volatile and non-volatile memory and/or storage elements), at least one input device, and at least one output device. For example and without limitation, the programmable computers may be a personal computer, laptop, personal data assistant, and cellular telephone, smart-phone device, tablet computer, and/or wireless device. Program code is applied to input data to perform the functions described herein and generate output information. The output information is applied to one or more output devices, in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM, magnetic disk, optical disk) readable by a general or special purpose programmable computer, for configuring and operating the computer when the storage media or device is read by the computer to perform the procedures described herein. The subject system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer usable instructions for one or more processors. The medium may be provided in various forms, including transitory and non-transitory forms, which include, but are not limited to, one or more diskettes, compact disks, tapes, chips, wireline transmissions, satellite transmissions, internet transmission or downloadings, magnetic and electronic storage media, digital and analog signals, and the like. The computer useable instructions may also be in various forms, including compiled and non-compiled code.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

FIG. 1A illustrates an example embodiment of a mammography system (100A). Mammography system (100A) may include any suitable processor (105) that is operatively coupled to memory (110). The memory (110) may store a plurality of physically scaled images ($130_1$) to ($130_n$) (where ($130_1$) represents a first image and ($130_n$) represents an nth image). The system (100A) may include a rendering module (115) for rendering a plurality of images ($130_1$) to ($130_n$), and a storage module ((120)) for storing a plurality of images ($130_1$) to ($130_n$) and instructions for the processor (105) on a database (125).

Images ($130_1$) to ($130_n$) stored by the storage module (120) may be mammography images. In some embodiments the images themselves may be stored in the memory (110) or the database (125) or both. In other embodiments, the images may be stored in computer readable storage media (not shown) such as magnetic or optical disc. In other embodiments, the image metadata such as image headers may also be stored in the database (125) wherein client devices (e.g. a digital imaging work station) may query the database for metadata information. The images ($130_1$) to ($130_n$) may be obtained from various imaging modalities, including an image projection on a single plane, overview images, rendered images (e.g. multi-planar reformatted images), or images derived from a series of spatially-related frames (e.g. in the case of a tomosynthesis image).

While database (125) is illustrated as residing in the memory (110) within the mammography system (100A), it will be understood that database (125) may be stored and accessed remotely through a network connection, for example, using a Digital Imaging and Communications in Medicine (DICOM) protocol over a network communications protocols known to those skilled in the art (e.g. HTTP, FTP, SFTP). In this case, it will be further understood that the operations of the rendering module (115) and storage module (120) may be performed locally on the mammography system, remotely on the system where the database (125) resides, or on a third-party system configured to access database (125) and mammography system (100).

Figure 1B:
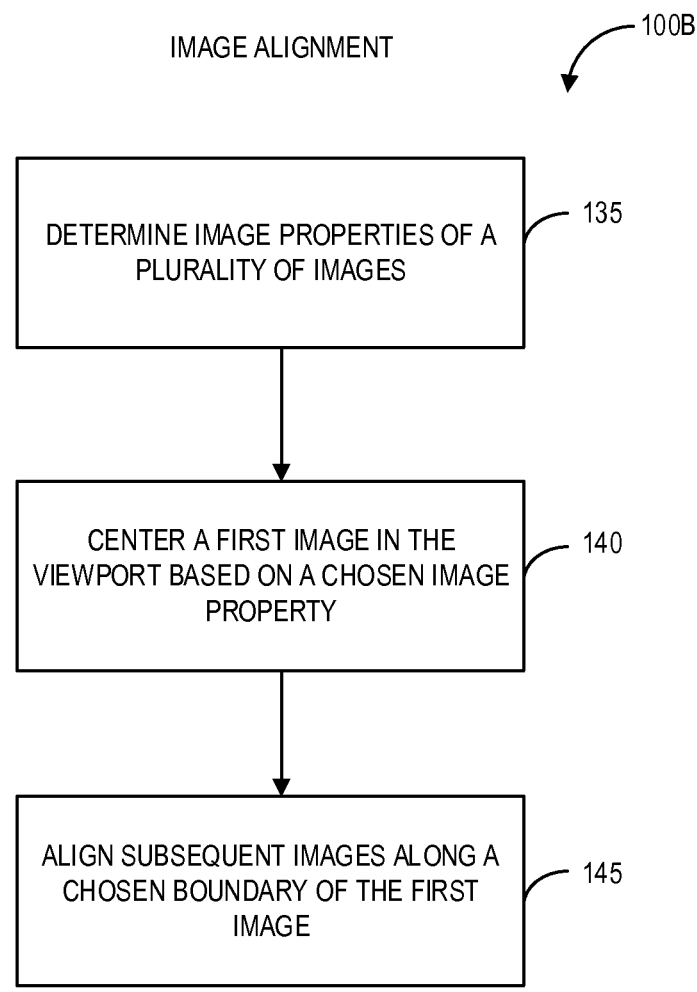
FIG. 1B is a flowchart diagram illustrating an alignment procedure.

Referring now to FIG. 1B, therein illustrated is a flowchart diagram (100B) illustrating the overall image alignment procedure performed by the processor (105) of the mammography system (100A). At step (135), at least one property (e.g. the mammographic view, image dimensions, etc.) is determined for each of the images ($130_1$) to ($130_n$). The processor (105) then selects a first image ($130_1$) based on the chosen property and centers the image in the viewport at step (140). Lastly, at step (145), subsequent images are aligned to the first image along a chosen boundary of the first image.

Figure 1C:
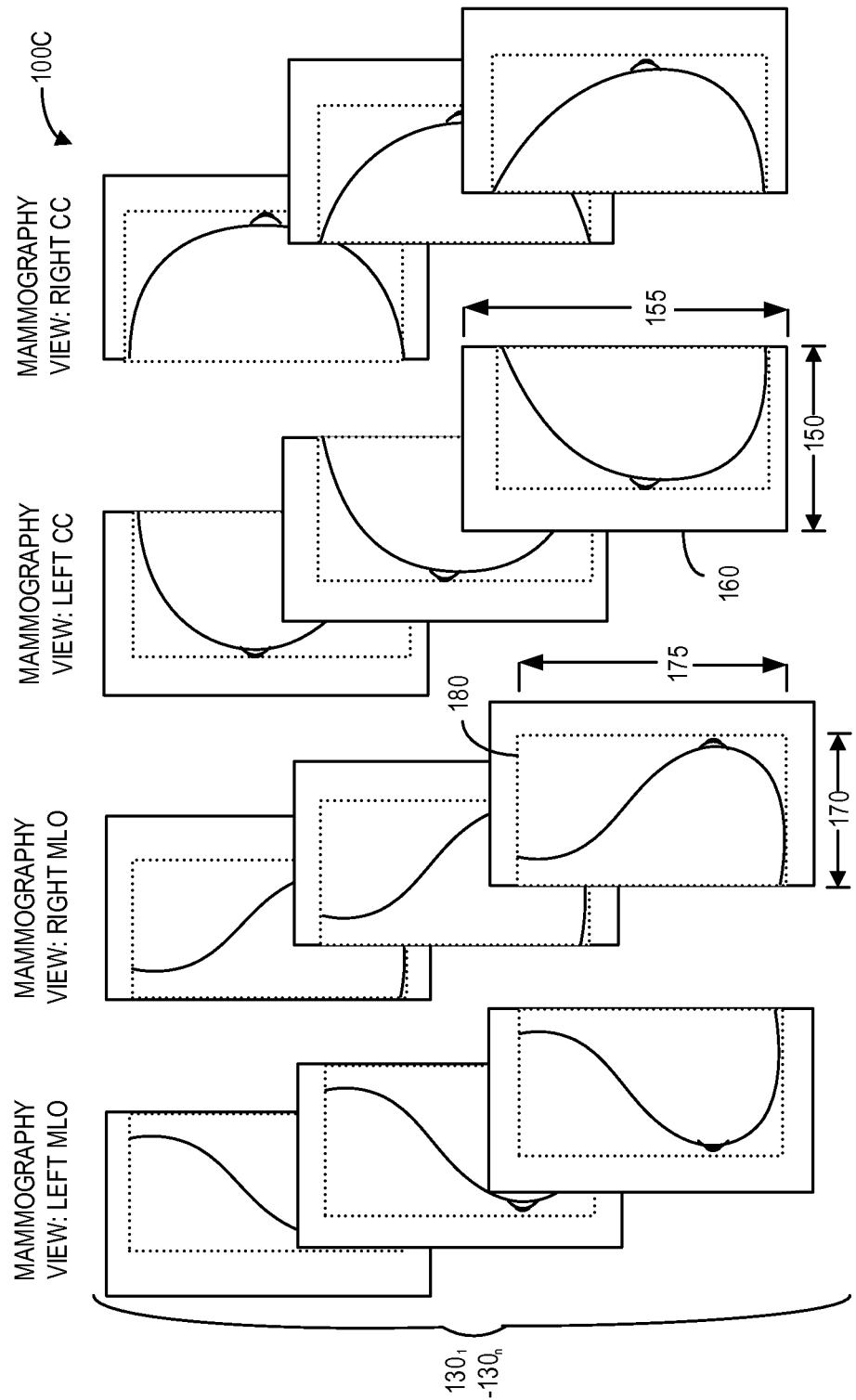
FIG. 1C is a schematic illustration of a plurality of mammographic images.

Referring now to FIG. 1C, therein illustrated is a schematic diagram (100C) of a plurality of images ($130_1$) to ($130_n$) stored by the storage module (120) in the database (125) within the mammography system (100A). Images ($130_1$) to ($130_n$) may comprise of images of the left breast, right breast, and both left and right breasts in the cranio-caudal ("CC") and/or medio-lateral oblique ("MLO") mammographic views. Additionally, images ($130_1$) to ($130_n$) may represent a collection of images acquired from a variety of sources. For example, the images may be digital scans of analog films, reconstructions of originally acquired images, and images acquired from a single imaging session and/or a series of imaging sessions spanning a defined period of time, wherein each imaging session may utilize a different image acquisition device. The images saved by the image acquisition device may include image header information containing image display settings associated with a specific display device or a common display device.

Image dimensions associated with the images ($130_1$) to ($130_n$) may be specified by referring to the image width (150) and image height (155) in association with the mammography image (160), or by referring to the breast image region width (170) or breast image region height (175) in association with the breast image region (180). In some embodiments, the breast image region (180) maybe defined as the image region whose width and height is determined by the widest breast feature and the highest breast feature, respectively. In another embodiment, the breast image region (180) may further be defined to encompass the largest frame of a multi-frame series of images such that the region encloses a projection of all frames onto a single parallel plane. In yet another embodiment, the breast image region (180) may be defined as the sub-region of a mammography image (160) which contains all breast tissue such that the region maximizes breast tissue depiction.

The boundaries of the mammography image or breast image region consist of a top boundary, a bottom boundary, a left boundary and a right boundary. Generally the top boundary, bottom boundary, left boundary and right boundary may refer to the top, bottom, left and right sides of the image, respectively, as it would appear on a viewport after manipulation according to prescribed hanging protocol rules.

Figure 2A:
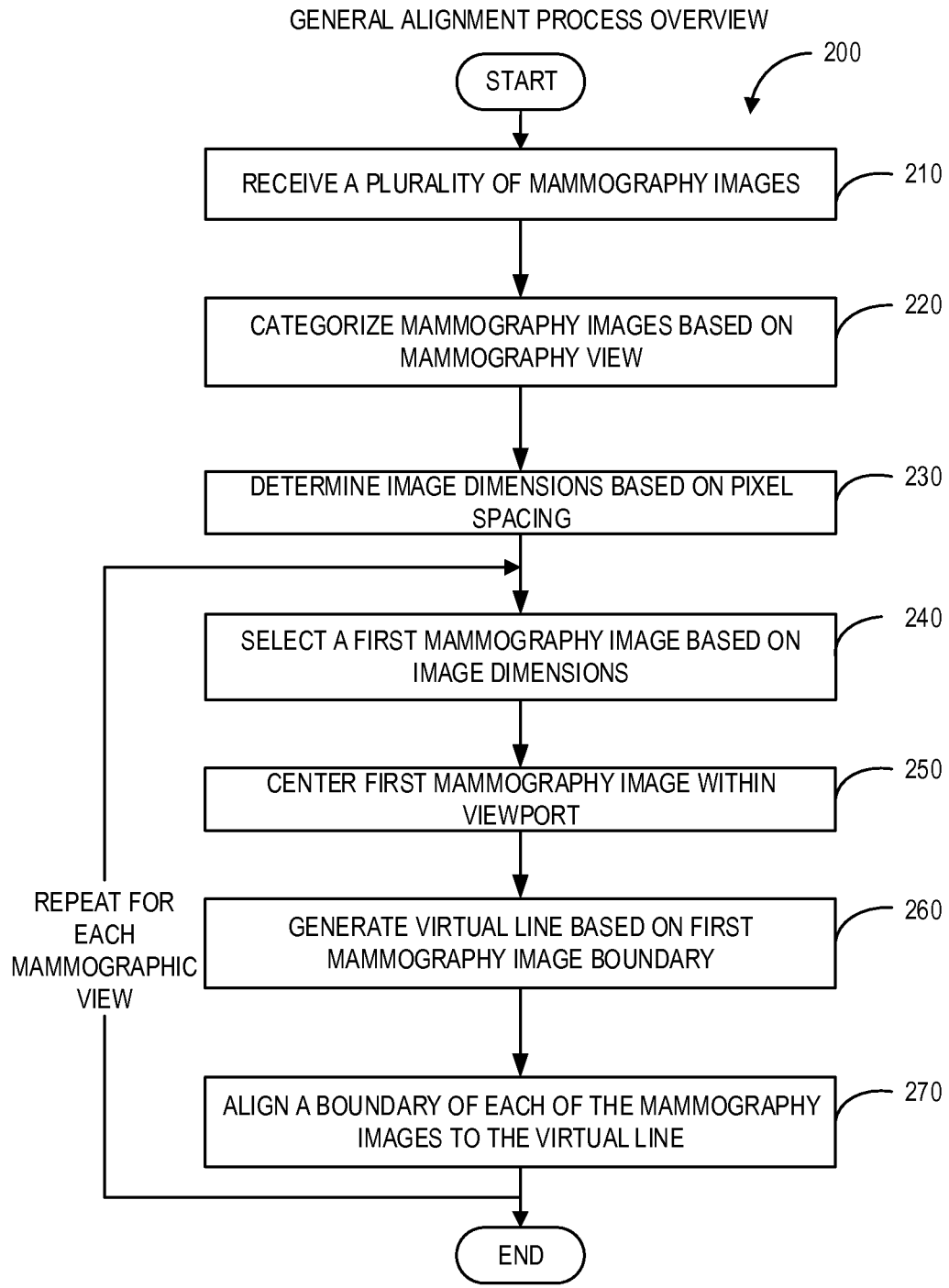
FIG. 2A is a flowchart diagram detailing the alignment process.
Figure 2B:
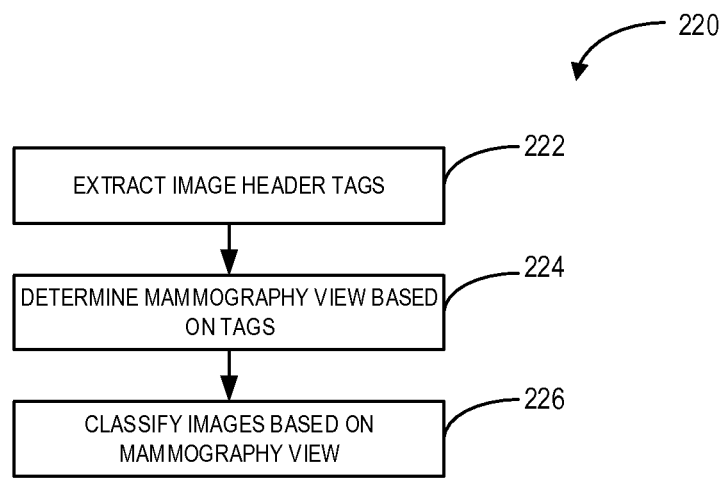
FIG. 2B is a flowchart diagram illustrating image categorization.
Figure 2C:
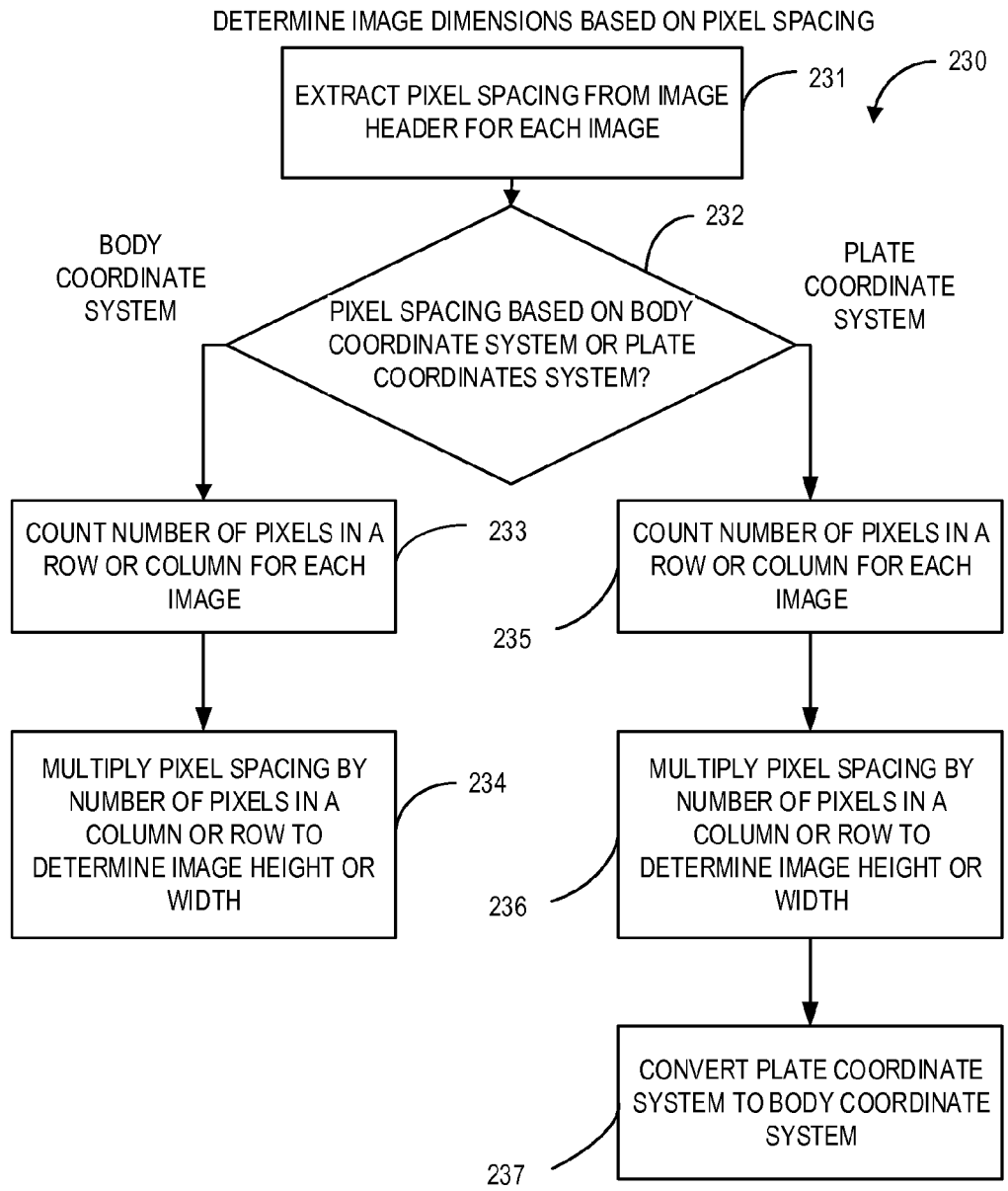
FIG. 2C is a flowchart diagram illustrating the determination of image dimensions.

FIGS. 2A to 2C are flowcharts illustrating in greater detail one embodiment of the image alignment process (200) performed by the mammography system (100).

Referring now to FIGS. 1A, 1B and 2A, the process begins at step (210) upon the mammography system (100) receiving a plurality of physically scaled mammography images (130₁) to (130ₙ). At step (220), the processor (105) of the mammography system (100) categorizes the images (130₁) to (130ₙ) based on a corresponding mammography view. In one embodiment, the processor (105) may categorize an image based on the mammographic view as either CC view or MLO view. At step (230), the processor (105) then determines the dimensions of the images (130₁) to (130ₙ) based on pixel spacing, as illustrated in more detail in FIG. 2C.

Having determined the dimensions and categorization of the images (130₁) to (130ₙ), the processor (105) proceeds to align the images (130₁) to (130ₙ) so as to allow comparison. Subsequent steps described in FIG. 2A, steps (240) to (270), are performed on each mammographic view.

Figure 3A:
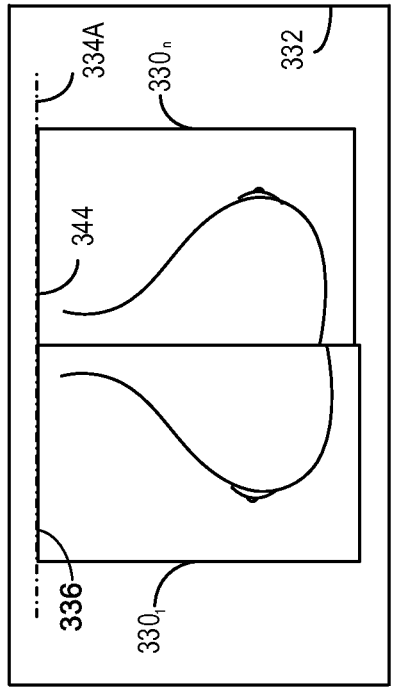
FIGS. 3A-3D are schematic illustrations showing vertical centering and alignment of mammography images in the MLO view.
Figure 3B:
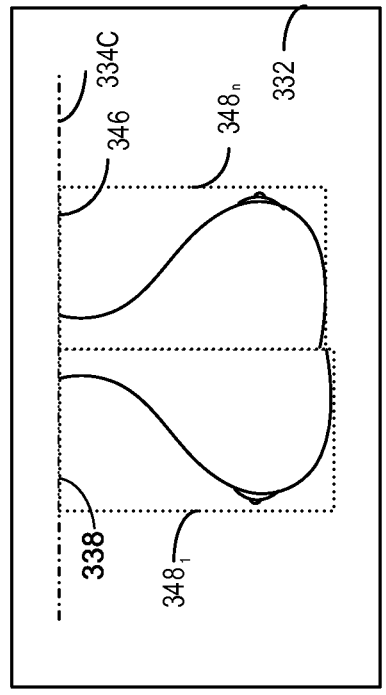
Figure 3C:
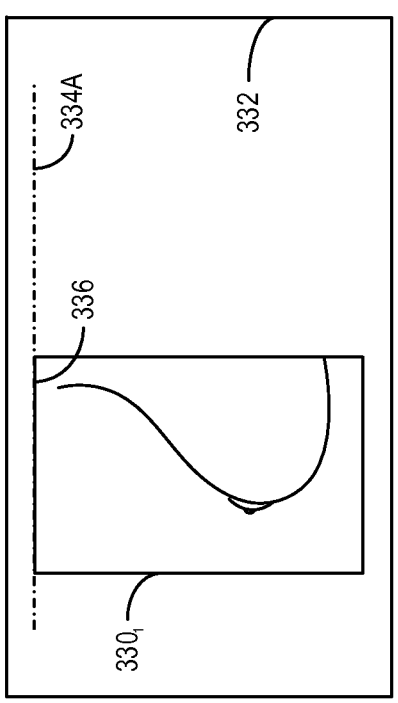

At step (240) the processor (105) selects a first image on the basis of image dimension. As will be explained further in FIG. 2C, image dimensions may be determined based on the image width (150) and image height (155), or breast image region width (170) and breast image region height (175). Using image dimension as a desired basis of selection, the first mammography image may be chosen from the collection of images on the basis that the chosen image has the largest width, height or both. For example, the first mammography image (330₁) illustrated in FIG. 3A may be chosen on the basis that it has the largest image height (155). In FIG. 3C, the first image (348₁) may be chosen on the basis that it has the largest breast image region height (175).

Figure 5A:
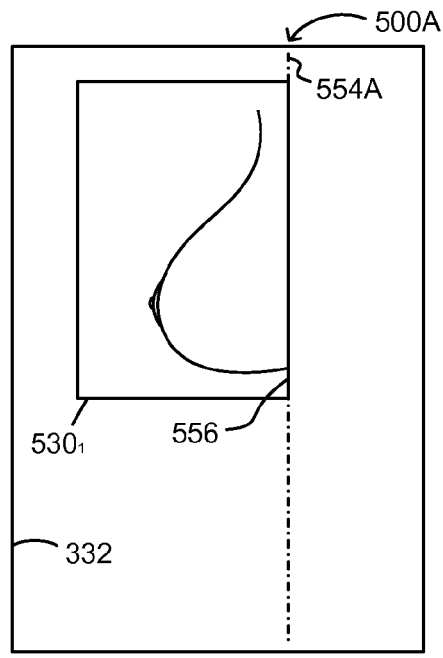
FIGS. 5A-5D are schematic illustrations showing horizontal centering and alignment of mammography images in the MLO view.

In step (250) the first mammography image is centered by the processor (105) within the viewport (332) and presented to the user by the rendering module (115). Centering of the first mammography image may be conducted with respect to either the horizontal axis or the vertical axis of the viewport (332). FIG. 3A provides an example of a vertically centered first image. FIG. 5A illustrates a horizontally centered first image.

In step (260), to facilitate alignment of subsequent images of the same category, a virtual line is generated based on a boundary of the first mammography image. In some embodiments, a virtual horizontal line may be generated along the top boundary of a vertically aligned image while a virtual vertical line maybe generated along the right boundary of a horizontally aligned image. FIG. 3A provides an example of a virtual horizontal line (334A) generated along the top boundary (336) of the vertically centered first mammography image 330₁. FIG. 5A provides an example of a virtual vertical line generated along the right boundary (556) of the horizontally centered first mammography image (530₁).

In step (270), subsequent images of the same category may be positioned with the first image such that a boundary of the subsequent image is aligned with the virtual line. As illustrated in FIG. 3B, the top boundary (344) of physically scaled mammography image (330ₙ) may be aligned to the generated virtual horizontal line (334A). As illustrated further in FIG. 5B, the right boundary (564) of physically scaled mammography image (530ₙ) is aligned to the generated virtual vertical line (554A).

Referring now to FIG. 2B, therein illustrated is a flowchart diagram of the process referred to in step (220) of FIG. 2A to categorize mammography images based on mammographic view. At step (222), the image header tags are extracted by the processor (105) after retrieving the images from the storage module (120). At step (224) the processor (105) determines the mammography view (e.g. CC view or MLO view) based on the extracted tags. At step (226), the processor (105) classifies the images according to the identified mammographic view.

Referring now to FIG. 2C, therein illustrated is a flowchart diagram of the process referred to in step (230) of FIG. 2A to determine image dimensions (width and height) based on pixel spacing. For example, the DICOM image format which is frequently used to digitally represent mammographic images, contain within the image header pixel spacing information. Pixel spacing may refer to the vertical spacing corresponding to the center-center distance between pixels of adjacent rows that belong to the same column, or horizontal spacing corresponding to the center-center distance between pixels of adjacent columns that belong to the same row. The pixel spacing may be specified with respect to the body coordinate system or the plate coordinate system. It is generally understood that the body coordinate system reflects distances measured as if they were made on the patient body, while the plate coordinate system refers to distances as measured on the imaging plate. In some embodiments, the mammographic system is configured to use the body coordinate system to represent image dimensions. Therefore images whose pixel spacing is based on plate coordinate system would require conversion to the body coordinate system before image comparisons can be made.

At step (231) of FIG. 2C, the processor (105) extracts pixel spacing information from the image header for each image. At step (232) the processor (105) determines whether the pixel spacing is based on the body coordinate system or plate coordinate system.

For pixel spacing based on the body coordinate system, the processor (105) at step (233) counts the number of pixels in a row or column for each image. At step (234) the processor (105) determines the image dimensions by multiplying the pixel spacing by the number of pixels in a column or row corresponding to the mammography image or breast image region to determine the width or height, respectively.

For pixel spacing based on the plate coordinate system, the processor (105) at step (235) counts the number of pixels in a row or column for each image. At step (236) the processor (105) determines the image dimensions by multiplying the pixel spacing by the number of pixels in a column or row corresponding to the mammography image or breast image region to determine image width or height, respectively. Finally, in step (237), the processor (105) converts the image dimensions from the plate coordinate system to the body coordinate system.

FIGS. 3A-3D, 4A-4D, 5A-5D and 6A-6D, illustrate examples of positioning and displaying images. The examples show that the mammography image or breast image region may be centered in a viewport with respect to the viewport's horizontal axis or vertical axis. While the figures depict images positioned adjacent to each other, it is understood that such an arrangement is one of many ways aligned images may be presented for comparison. For instance, in some embodiments, the plurality of images may be aligned and arranged in a stack within a viewport so that images may appear before or behind each other to allow the medical personnel to examine a series of aligned images by "scrolling" through a sequence of aligned images with a peripheral device such as a computer mouse. In yet another embodiment, a combination of the previously mentioned arrangements may be used to facilitate image comparison. For instance, multiple viewports may be aligned according to a virtual line with each viewport presenting images arranged in stacks.

FIGS. 3A and 3B illustrate vertical alignment of mammographic images in the MLO view. Referring now to FIG. 3A, therein illustrated is a schematic diagram of a first mammography image ($330_1$) in the MLO view vertically centered within the viewport (332). Vertically centering the first mammography image ($330_1$) may be accomplished by positioning the first mammography image ($330_1$) within the viewport (332) such that the vertical space above and below the first mammography image ($330_1$) within the viewport (332) are equal. With the first mammography image ($330_1$) vertically centered, a virtual horizontal line (334A) may be generated corresponding to the top boundary (336) of the first physically scaled mammography image.

Referring now to FIG. 3B, therein illustrated is a schematic diagram of a mammography image ($330_n$) in the MLO view positioned within the viewport (332) adjacent to the first mammography image ($330_1$) such that the top boundary (344) of the mammography image ($330_n$) is aligned with the virtual horizontal line (334A).

Figure 3D:
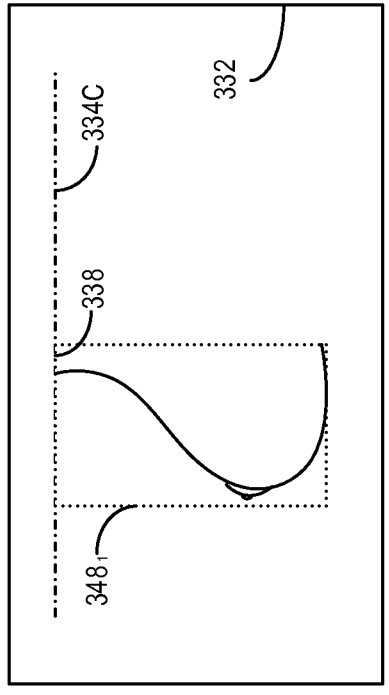

FIGS. 3C and 3D illustrate vertical alignment of mammographic images in the MLO view based on the breast image region. Referring now to FIG. 3C, therein illustrated is a schematic diagram of a first breast image region ($348_1$) in the MLO view vertically centered within the viewport (332). Vertically centering the first breast image region ($348_1$) may be accomplished by positioning the first breast image region ($348_1$) within the viewport (332) such that the vertical space above and below the first breast image region ($348_1$) within the viewport (332) are equal. With the first breast image region ($348_1$) vertically centered, a virtual horizontal line (334C) may be generated corresponding to the top boundary (338) of the first breast image region ($348_1$).

Referring now to FIG. 3D, therein illustrated is a schematic diagram of a breast image region ($348_n$) in the MLO view positioned within the viewport (332) adjacent to the first breast image region ($348_1$) such that the top boundary (346) of the breast image region ($348_n$) is aligned with the virtual horizontal line (334C).

Figure 4A:
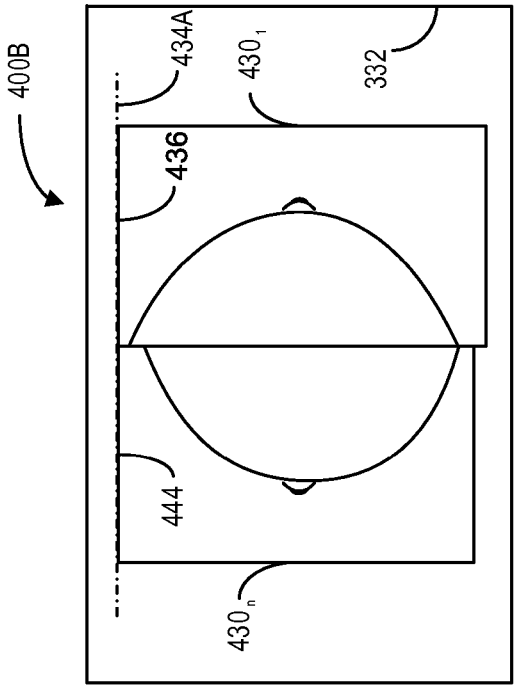
FIGS. 4A-4D are schematic illustrations showing vertical centering and alignment of mammography images in the CC view.
Figure 4B:
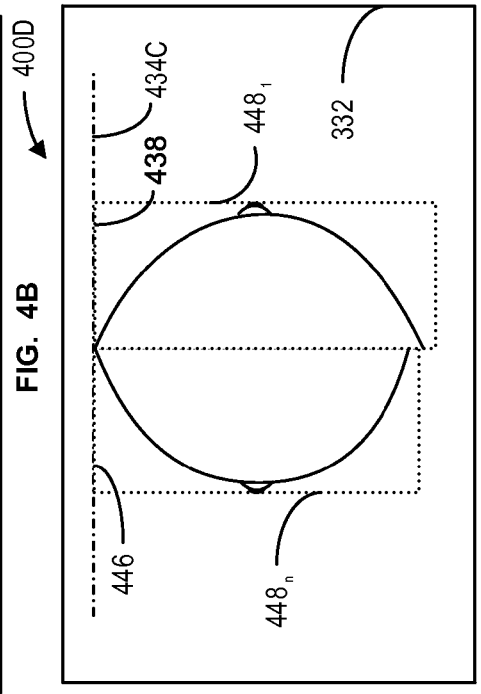

FIGS. 4A and 4B illustrate vertical alignment of mammographic images in the CC view. Referring now to FIG. 4A, therein illustrated is a schematic diagram of a first mammography image ($430_1$) in the CC view vertically centered within the viewport (332). Vertically centering the first mammography image ($430_1$) may be accomplished by positioning the first mammography image ($430_1$) within the viewport (332) such that the vertical space above and below the first mammography image ($430_1$) within the viewport (332) are equal. With the first mammography image ($430_1$) vertically centered, a virtual horizontal line (434A) may be generated corresponding to the top boundary (436) of the first physically scaled mammography image.

Referring now to FIG. 4B, therein illustrated is a schematic diagram of a mammography image ($430_n$) in the CC view positioned within the viewport (332) adjacent to the first mammography image $430_1$ such that the top boundary (444) of the mammography image ($430_n$) is aligned with the virtual horizontal line (434A).

Figure 4C:
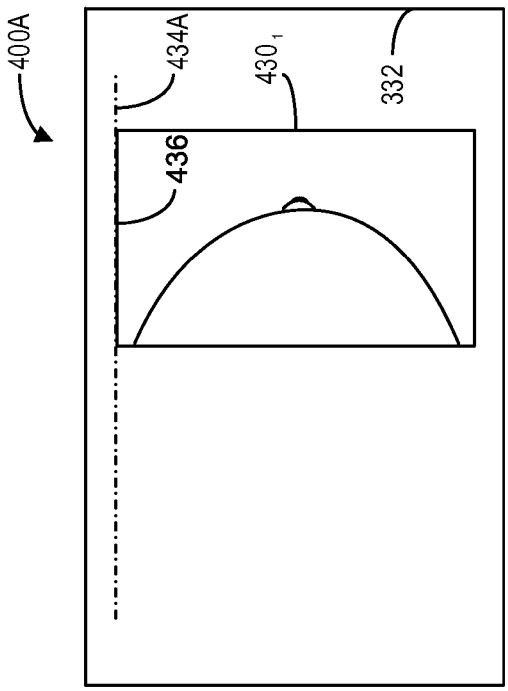
Figure 4D:
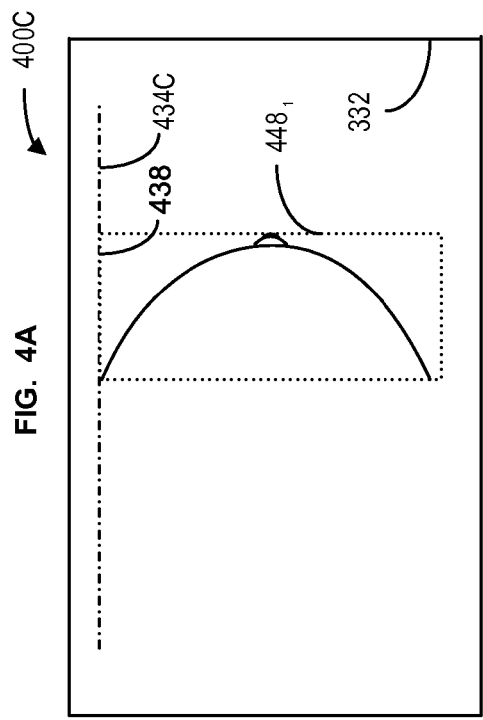

FIGS. 4C and 4D illustrate vertical alignment of mammographic images in the CC view based on the breast image region. Referring now to FIG. 4C, therein illustrated is a schematic diagram of a first breast image region ($448_1$) in the CC view vertically centered within the viewport (332). Vertically centering the first breast image region ($448_1$) may be accomplished by positioning the first breast image region ($448_1$) within the viewport (332) such that the vertical space above and below the first breast image region ($448_1$) within the viewport (332) are equal. With the first breast image region ($448_1$) vertically centered, a virtual horizontal line (434C) may be generated corresponding to the top boundary (438) of the first breast image region ($448_1$).

Referring now to FIG. 4D, therein illustrated is a schematic diagram of a breast image region ($448_n$) in the CC view positioned within the viewport (332) adjacent to the first breast image region ($448_1$) such that the top boundary (446) of the breast image region ($448_n$) is aligned with the virtual horizontal line (434C).

Figure 5B:
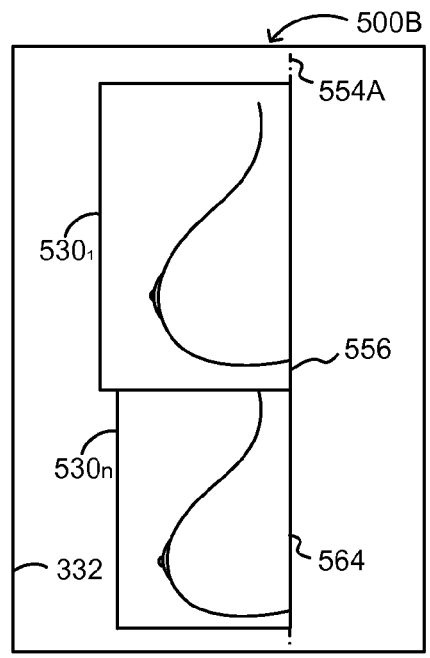

FIGS. 5A and 5B illustrate horizontal alignment of mammographic images in the MLO view. Referring now to FIG. 5A, therein illustrated is a schematic diagram of a first mammography image ($530_1$) in the MLO view horizontally centered within the viewport (332). Horizontally centering the first mammography image ($530_1$) may be accomplished by positioning the first mammography image ($530_1$) within the viewport (332) such that the horizontal space to the left and right the first mammography image ($530_1$) within the viewport (332) are equal. With the first mammography image ($530_1$) horizontally centered, a virtual vertical line (554A) may be generated corresponding to the right boundary (556) of the first physically scaled mammography image.

Referring now to FIG. 5B, therein illustrated is a schematic diagram of a mammography image ($530_n$) in the MLO view positioned within the viewport (332) adjacent to the first mammography image $530_1$ such that the right boundary (564) of the mammography image ($530_n$) is aligned with the virtual vertical line (554A).

Figure 5C:
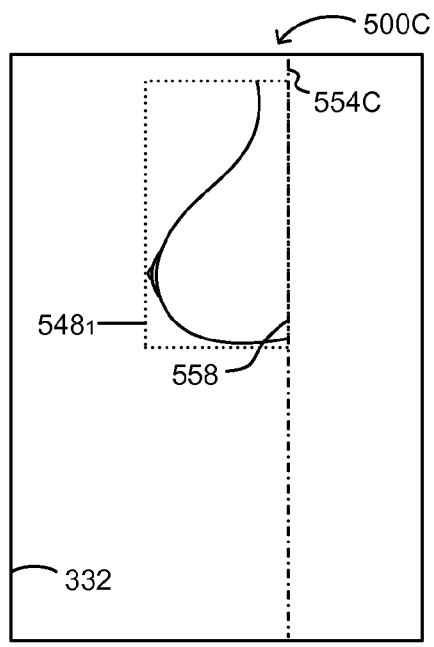
Figure 5D:
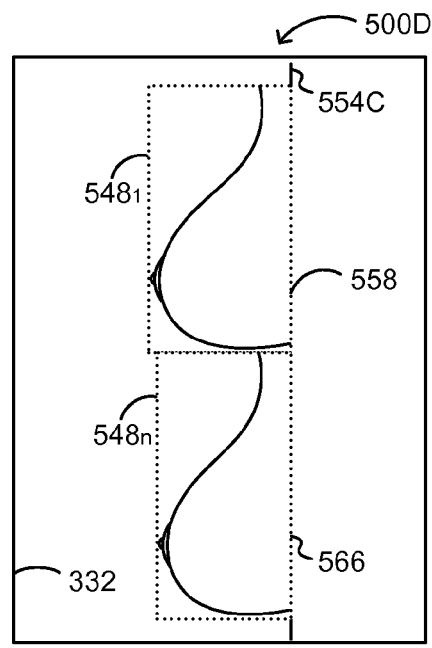

FIGS. 5C and 5D illustrate horizontal alignment of mammographic images in the MLO view based on the breast image region. Referring now to FIG. 5C, therein illustrated is a schematic diagram of a first breast image region ($548_1$) in the MLO view horizontally centered within the viewport (332). Horizontally centering the first breast image region ($548_1$) may be accomplished by positioning the first breast image region ($548_1$) within the viewport (332) such that the horizontal space to the left and right of the first breast image region ($548_1$) within the viewport (332) are equal. With the first breast image region ($448_1$) horizontally centered, a virtual vertical line (554C) may be generated corresponding to the right boundary (558) of the first breast image region ($548_1$).

Referring now to FIG. 5D, therein illustrated is a schematic diagram of a breast image region ($548_n$) in the MLO view positioned within the viewport (332) adjacent to the first breast image region ($548_1$) such that the right boundary (566) of the breast image region ($548_n$) is aligned with the virtual vertical line (554C).

Figure 6A:
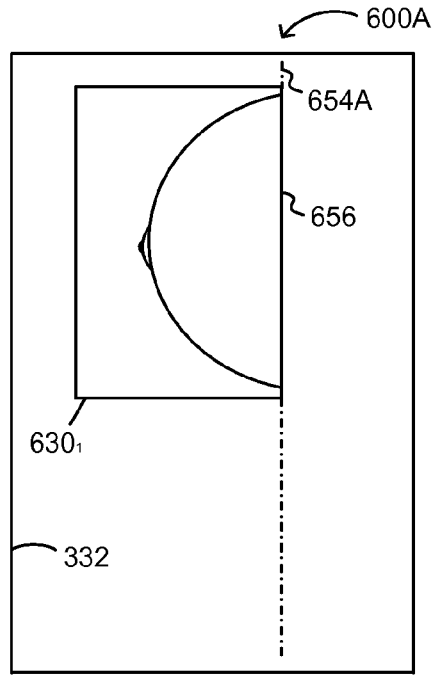
FIGS. 6A-6D are schematic illustrations showing horizontal centering and alignment of mammography images in the CC view.
Figure 6B:
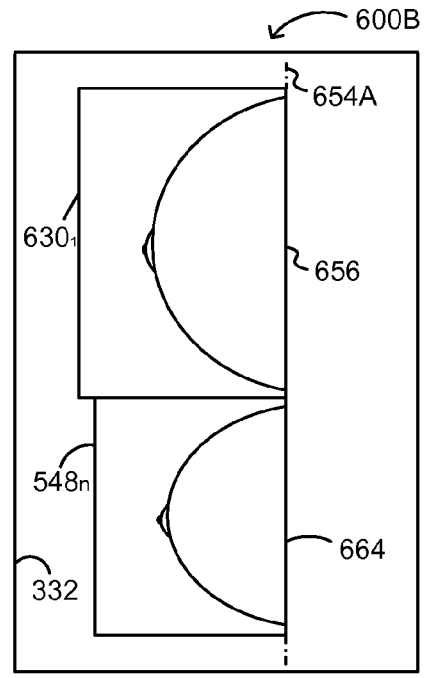

FIGS. 6A and 6B illustrate horizontal alignment of mammographic images in the CC view. Referring now to FIG. 6A, therein illustrated is a schematic diagram of a first mammography image ($630_1$) in the CC view horizontally centered within the viewport (332). Horizontally centering the first mammography image ($630_1$) may be accomplished by positioning the first mammography image ($630_1$) within the viewport (332) such that the horizontal space to the left and right of the first mammography image ($630_1$) within the viewport (332) are equal. With the first mammography image ($630_1$) horizontally centered, a virtual vertical line (654A) may be generated corresponding to the right boundary (656) of the first physically scaled mammography image.

Referring now to FIG. 6B, therein illustrated is a schematic diagram of a mammography image ($630_n$) in the CC view positioned within the viewport (332) adjacent to the first mammography image $630_1$ such that the right boundary (664) of the mammography image ($630_n$) is aligned with the virtual vertical line (654A).

Figure 6C:
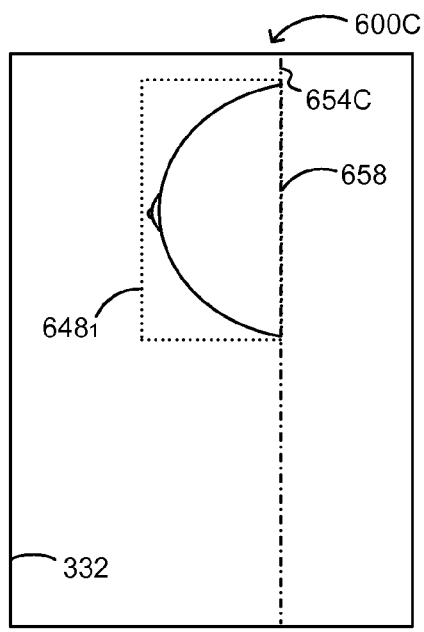
Figure 6D:
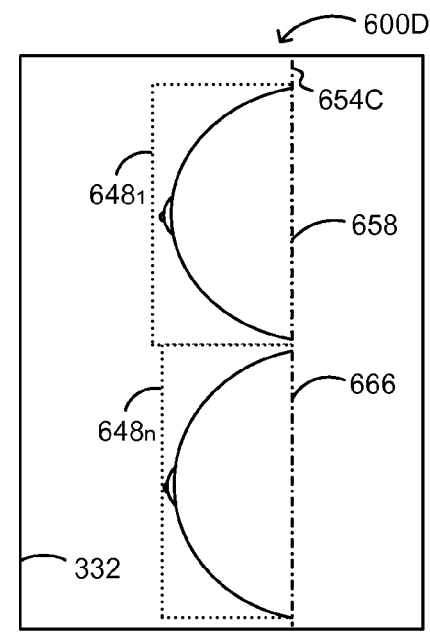

FIGS. 6C and 6D illustrate horizontal alignment of mammographic images in the CC view based on the breast image region. Referring now to FIG. 6C, therein illustrated is a schematic diagram of a first breast image region ($648_1$) in the CC view horizontally centered within the viewport (332). Vertically centering the first breast image region ($648_1$) may be accomplished by positioning the first breast image region ($648_1$) within the viewport (332) such that the horizontal space to the left and right of the first breast image region ($648_1$) within the viewport (332) are equal. With the first breast image region ($648_1$) horizontally centered, a virtual vertical line (654C) may be generated corresponding to the right boundary (658) of the first breast image region ($648_1$).

Referring now to FIG. 6D, therein illustrated is a schematic diagram of a breast image region ($648_n$) in the CC view positioned within the viewport (332) adjacent to the first breast image region ($648_1$) such that the right boundary (666) of the breast image region ($648_n$) is aligned with the virtual vertical line (654C).

While the above description provides examples of the embodiments, it will be appreciated that some features and/or functions of the described embodiments are susceptible to modification without departing from the spirit and principles of operation of the described embodiments. Accordingly, what has been described above has been intended to be illustrative of the invention and non-limiting and it will be understood by persons skilled in the art that other variants and modifications may be made without departing from the scope of the invention as defined in the claims appended hereto.

It will be appreciated that while the present invention has been described in the context of medical image management in order to provide an application-specific illustration, it should be understood that the method and system presented could also be applied to any other type of image review and analysis system.

Numerous specific details are set forth herein in order to provide a thorough understanding of the exemplary embodiments described herein. However, it will be understood by those of ordinary skill in the art that these embodiments may be practiced without these specific details. In other instances, well-known methods, procedures and components have not been described in detail so as not to obscure the description of the embodiments.

While the invention has been disclosed in connection with certain preferred embodiments, this should not be taken as a limitation to all of the provided details. Modifications and variations of the described embodiments may be made without departing from the spirit and scope of the invention, and other embodiments should be understood to be encompassed in the present disclosure as would be understood by those of ordinary skill in the art.

The invention claimed is:

1. A method for aligning a plurality of physically scaled mammography images within at least one viewport, the method comprising:
   categorizing each of the plurality of physically scaled mammography images based on a corresponding mammography view;
   determining image dimensions of each of the plurality of physically scaled mammography images based on pixel spacing;
   selecting a first mammography image from the plurality of physically scaled mammography images for each corresponding mammography view based on the image dimensions;
   centering the first mammography image within the at least one viewport;
   generating a virtual line across the at least one viewport based on a boundary of the first mammography image; and
   aligning each of the plurality of physically scaled mammography images corresponding to the mammography view such that a boundary of each of the plurality of physically scaled mammography images is aligned with the virtual line.

2. The method of claim 1, wherein the first mammography image is vertically centered within the viewport.

3. The method of claim 1, wherein the virtual line is a horizontal virtual line.

4. The method of claim 1, wherein the boundary of the first mammography image consists of one of the following: a top boundary, a bottom boundary, a left boundary, and a right boundary.

5. The method of claim 1, wherein the boundary of each of the plurality of physically scaled images consists of one of the following: a top boundary, a bottom boundary, a left boundary, and a right boundary.

6. The method of claim 1, wherein the plurality of physically scaled mammography images in the corresponding mammography view contains at least one right mammography image associated with at least one left mammography image, and wherein aligning each of the plurality of physically scaled mammography images further comprises aligning the at least one right mammography image with the at least one associated left mammography image.

7. The method of claim 1, wherein the image dimensions are selected from a group consisting of: image height and image width.

8. The method of claim 1, wherein the first mammography image is selected based on the largest image dimensions.

9. The method of claim 1, wherein the plurality of mammography images each comprise a breast image region and wherein the image dimensions are determined based on the breast image region.

10. The method of claim 1, wherein the plurality of mammography images include a first temporal image and an associated second temporal image, and wherein aligning each of the plurality of mammography images further comprises aligning the first temporal image with the associated second temporal image.

11. The method of claim 1, wherein pixel spacing is based on one of the following: a patient body coordinate system and a plate coordinate system.

12. A physical non-transitory computer readable medium comprising instructions for aligning a plurality of physically scaled mammography images within at least one viewport, the instructions comprising:
- categorizing each of the plurality of physically scaled mammography images based on a corresponding mammography view;
- determining image dimensions of each of the plurality of physically scaled mammography images based on pixel spacing;
- selecting a first mammography image from the plurality of physically scaled mammography images for each corresponding mammography view based on the image dimensions;
- centering the first mammography image within the at least one viewport;
- generating a virtual line across the at least one viewport based on a boundary of the first mammography image; and
- aligning each of the plurality of physically scaled mammography images corresponding to the mammography view such that a boundary of each of the plurality of physically scaled mammography images is aligned with the virtual line.

13. The physical non-transitory computer readable medium of claim 12, wherein the first mammography image is vertically centered within the viewport.

14. The physical non-transitory computer readable medium of claim 12, wherein the virtual line is a horizontal virtual line.

15. A system for aligning a plurality of physically scaled mammography images within at least one viewport, the system comprising:
- a memory for the plurality of physically scaled breast images;
- a processor configured to:
  - categorize each of the plurality of physically scaled mammography images based on a corresponding mammography view;
  - determine image dimensions of each of the plurality of physically scaled mammography images based on pixel spacing;
  - select a first mammography image from the plurality of physically scaled mammography images for each corresponding mammography view based on the image dimensions;
  - center the first mammography image within the at least one viewport;
  - generate a virtual line across the at least one viewport based on a boundary of the first mammography image; and
  - align each of the plurality of physically scaled mammography images corresponding to the mammography view such that a boundary of each of the plurality of physically scaled mammography images is aligned with the virtual line.

16. The system of claim 15, wherein the first mammography image is vertically centered within the viewport.

17. The system of claim 15, wherein the virtual line is a horizontal virtual line.

* * * * *